United States Patent
Marcy et al.

(10) Patent No.: US 9,486,418 B2
(45) Date of Patent: Nov. 8, 2016

(54) METHOD FOR TREATING OR PREVENTING DRY EYE DISORDERS USING ALKYLAMINO-POLYHYDROXYALKANES

(75) Inventors: Alice Marcy, Doylestown, PA (US); Annette M. Tobia, Wyndmoor, PA (US)

(73) Assignee: Dynamis Pharmaceuticals, Inc., Jenkintown, PA (US)

( * ) Notice: Subject to any disclaimer, the term of this patent is extended or adjusted under 35 U.S.C. 154(b) by 966 days.

(21) Appl. No.: 12/420,374

(22) Filed: Apr. 8, 2009

(65) Prior Publication Data

US 2009/0253804 A1    Oct. 8, 2009

Related U.S. Application Data

(60) Provisional application No. 61/043,162, filed on Apr. 8, 2008.

(51) Int. Cl.
*A61K 31/133* (2006.01)

(52) U.S. Cl.
CPC .................................. *A61K 31/133* (2013.01)

(58) Field of Classification Search
CPC .................................................... A61K 31/133
See application file for complete search history.

(56) References Cited

U.S. PATENT DOCUMENTS

| | | | |
|---|---|---|---|
| 7,732,611 B2 * | 6/2010 | Nishioka et al. | 546/159 |
| 2007/0155787 A1 | 7/2007 | Nishioka et al. | |
| 2008/0090841 A1 * | 4/2008 | Johnson et al. | 514/255.06 |

* cited by examiner

*Primary Examiner* — Zohreh Fay
(74) *Attorney, Agent, or Firm* — Patrick J. Hagan; Dann, Dorfman, Herrell and Skillman

(57) ABSTRACT

Method for the treatment or prophylaxis of dry eye disorders by the administration of alkylamino-polyhydroxyalkanes and compositions thereof.

11 Claims, 1 Drawing Sheet

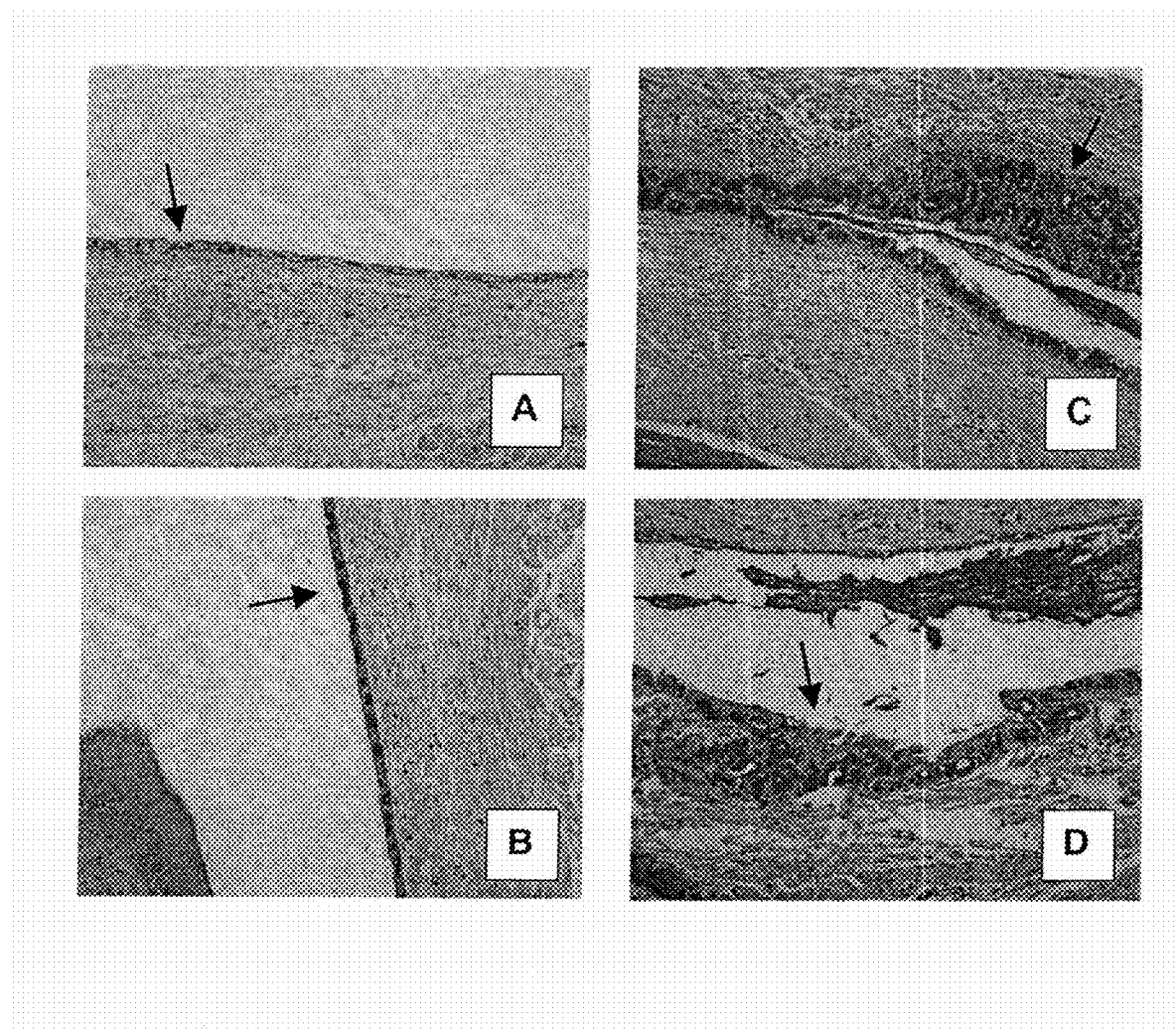

METHOD FOR TREATING OR PREVENTING DRY EYE DISORDERS USING ALKYLAMINO-POLYHYDROXYALKANES

CROSS-REFERENCE TO RELATED APPLICATIONS

The present application claims the benefit of U.S. Provisional Patent Application No. 61/043,162, filed Apr. 8, 2008, the entire disclosure of which is incorporated by reference herein.

FIELD OF THE INVENTION

The present invention relates to the use of certain alkylamino-polyhydroxyalkanes for the treatment or prevention of dry eye disorders.

BACKGROUND OF THE INVENTION

The eye surface is kept moist by a tear film composed of an oily layer, a watery layer and a layer of mucus. The outermost oily layer is produced by the meibomian glands and reduces tear evaporation. The middle layer is the watery liquid typical of tears and is produced by lacrimal glands. The inner layer of mucus is produced by goblet cells in the conjunctiva, and enables the watery layer to evenly coat the eye. Mucins are the main component of mucus and have an important role in maintaining the aqueous and oily layers of the eye film.

Dry eye (keratoconjunctivitis sicca or keratitis sicca) is a chronic dryness of the corneal and conjunctival surfaces and results from a decrease in the production of tear components or from an altered ratio of the individual oil, water and mucus components to each other. People with dry eye have various symptoms including redness, soreness, burning, itching, photophobia, blurred vision, foreign body sensation (grittiness) and contact lens intolerance. Environmental conditions can worsen these symptoms.

Dry eye can be a side effect caused by certain drugs such as diuretics, beta blockers, antihistamines, sleeping pills, or pain relievers. The LASIK (laser assisted in situ keratomileusis) procedure can cause dry eye due to corneal denervation (Toda, 2007). Several hormones impact tear component production and hormone insufficiency can cause dry eye (Sullivan, 2004). The prevalence of dry eye increases with age and is higher among women (Moss et al. 2000).

Dry eye can be classified as either tear production deficient or evaporative dry eye (Lemp, 1995). The former includes Sjogren-associated and non-Sjogren associated dry eye. Sjogren's disease is an autoimmune syndrome of the exocrine glands that includes dry eyes and dry mouth (Srinvassan and Siomovic, 2007). In both of these conditions, there is an inflammatory environment characterized by T cell infiltration of the conjunctiva, and increased levels of the inflammatory cytokines tumor necrosis factor (TNF), interleukin 1 alpha (IL-1a), IL-6, IL-8 and IL-10 (Zoukhri, 2006). These factors result in alterations of the conjunctival epithelia, a loss of goblet cells and a decrease in mucin production.

Current therapies for dry eye include the use of artificial tears to rehydrate the ocular surface and provide symptomatic relief. Their benefits are short lived, however, and frequent dosing is required. Other therapies include steroids (U.S. Pat. No. 5,958,912), cyclosporine A (Tauber, 1998), hydroxyeicosatetraenoic acid derivatives (U.S. Pat. No. 5,696,166), adenine analogues (Jumblatt and Jumblatt, 1998), purinergic receptor antagonists (U.S. Pat. No. 5,900,407), phosphodiesterase inhibitors (U.S. Pat. No. 4,753,945), glycosides (U.S. Pat. No. 7,223,737), melanocyte stimulating hormones (U.S. Pat. No. 4,868,154), and conjugated estrogens (U.S. Pat. No. 5,041,434).

Goblet cells are the primary source of excreted mucin. The cornea and conjunctival epithelial cells also produce transmembrane mucin to maintain a hydrated surface. Lacrimal cells produce a small soluble mucin. Dry eye causes changes in both the secreted and membrane-associated mucins (Gipson et al. 2004). Release of mucin from conjunctival cells is regulated by neurotransmitters.

There is an interest in treating dry eye with agents that can increase mucin production. Nicotinic receptor agonists have been reported to stimulate conjunctival cells to secrete mucin (U.S. Pat. No. 6,277,855). The purinoreceptor P2Y$_2$ agonist INS365 increased goblet cell density in a rat model of dry eye (Fujihara et al., 2001). Some anti-ulcer drugs stimulate mucus secretion. The anti-ulcer drug gefarnate increases conjunctival goblet cell density in a rabbit model of dry eye (Nakamura et al. 1998). Hormone replacement therapy for post-menopausal women causes an increase in conjunctival goblet cell density (Pelit et al. 2003). Cyclosporine treatment results in an increase in goblet cell numbers in patients with dry eye (Kunert et al. 2002).

As goblet cells are present in other tissues (digestive and respiratory epithelia; agents that increase mucin production may have additional utilities in treating conditions such as constipation, anorexia, dry mouth (xerostomia) and respiratory pathologies (Shimotoyodome et al., 2000; Deplancke and Gaskins, 2001).

SUMMARY OF THE INVENTION

In accordance with one embodiment, the present invention provides a method of treating or preventing dry mucus membrane disorders that can be alleviated by increasing mucin production, e.g., dry eyes, dry mouth and age-related constipation in a patient in need thereof by administering to the patient a therapeutically or prophylactically effective amount of a compound having the formula:

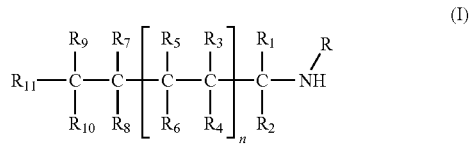

wherein R represents a substituted or unsubstituted alkyl ($C_1$-$C_4$), said alkyl substituents being selected from the group of hydroxy, carboxy, and phosphono substituents;

$R_1$ and $R_2$ are the same or different and represent a radical selected from the group consisting of hydrogen and hydroxymethyl radicals;

$R_3$ and $R_4$ are the same or different and represent a hydrogen or hydroxy radical;

$R_5$ and $R_6$ are different and represent either a hydrogen or hydroxy radical;

$R_7$ and $R_8$ are different and represent either a hydrogen or hydroxy radical;

$R_9$, $R_{10}$ and $R_{11}$ are the same or different and represent a radical selected from the group consisting of hydrogen, alkyl ($C_1$-$C_2$), hydroxyalkyl and hydroxy radicals;

n represents either 0 or 1;

the pharmaceutical acceptable salts and isomeric forms of said compound.

In another embodiment, this invention provides a method of for prophylaxis of dry eye disorders in a patient in need of thereof, the method comprising administering to the patient a prophylactically effective amount of a compound of formula I, above.

BRIEF DESCRIPTION OF THE DRAWING

FIG. 1 shows examples of goblet cell densities for eye tissues from scopolamine dosed animals treated with either a saline eyemist (panels A and B) or oral meglumine (panels C and D). The animals on oral meglumine (panels) have more extensive regions containing goblet cells.

DETAILED DESCRIPTION OF THE INVENTION

Although the method of the present invention is applicable to a range of dry mucus membrane disorders, it will be described hereinbelow with particular emphasis on the treatment of dry eyes.

A representative example of the synthesis of hydrochloride salts of the above alkylamino-polyhydroxyalkanes is as follows:

An aldose or ketose sugar (2 mmol) is dissolved in 10 ml of methanol and an appropriate amine (1.5 mmol) in methanol is added followed by 1 ml of a slurry of activated Raney nickel. This is shaken under 28 psi of hydrogen for 18 hours. The catalyst is removed by filtration and the filtrate evaporated. The residue is dissolved in 2 ml of water and purified by ion-exchange chromatography on a Dowex-50 column (1×10 cm). The column is washed with water to remove excess sugar and the product eluted with a linear gradient of 0 to 10% ammonium hydroxide (50 ml). Evaporation of the ammonia yields the free base which is converted to its hydrochloride salt by neutralizing with 1N HCL. Evaporation of the solvent yields the hydrochloride salt of the alkylamino-polyhydroxyalkane.

The compounds represented by formula I, above, are intended to include all possible isomeric forms thereof including structural isomers and stereoisomers or conformational isomers.

The compounds described herein can form pharmaceutically acceptable salts with various inorganic or organic acids or bases. Suitable bases include, e.g., alkali metal salts, alkaline earth metal salts, ammonium, substituted ammonium and other amine salts. Suitable acids include, e.g., hydrochloric acid, hydrobromic acid and methanesulfonic acid.

The pharmaceutically acceptable salts of the compounds of formula I can be prepared following procedures which are familiar to those skilled in the art.

The above-described compounds and their pharmaceutically acceptable salts can be used to prepare pharmaceutical compositions which also comprise a pharmaceutically acceptable carrier medium or auxiliary agent.

The pharmaceutical composition may be prepared in various forms for administration, including both liquids and solids. Thus, the composition may be in the form of tablets, caplets, pills or dragees, or can be filled in suitable containers, such as capsules, or, in the case of solutions or suspensions, filled into bottles. As used herein, "pharmaceutically acceptable carrier medium" includes any and all solvents, diluents, buffers or other liquid vehicle, dispersion or suspension aids, surface active agents, tonicity agents, viscosity modifiers, e.g., thickening or emulsifying agents, preservatives, antimicrobial agents, solid binders, lubricants, dissolution aids and the like, as suited to the particular dosage form desired. Representative examples of suitable carrier media include gelatine, lactose, starch, magnesium stearate, talc, vegetable and animal fats and oils, gums, polyalkylene glycol, water, or the like. *Remington: The Science and Practice of Pharmacy*, 20th Edition, A. R. Gennaro et al. (Lippincott, Williams & Wilkins, Baltimore, Md. (2000)) discloses various carriers used in formulating pharmaceutical compositions, e.g., for topical ophthalmic and oral administration, as well as known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention.

In the pharmaceutical composition of the invention, the active agent(s) may be present in an amount of at least 0.0001% and generally not more than about 10.0% by weight, based no the total weight of the composition, including carrier medium and/or auxiliary agent(s), if any. Preferably, the proportion of active agent varies between 0.001%-0.01% by weight of the composition. One or more supplementary active agent may also be included in the pharmaceutical compositions of this invention. For example, steroids, cyclosporine A, hydroxyeicosatetraenoic acid derivatives, adenine analogues, purinergic receptor antagonists, phosphodiesterase inhibitors, glycosides, melanocyte stimulating hormones, purinoreceptor $P2Y_2$ agonists, or conjugated estrogens may be used as a supplementary active agent for the purpose of preventing loss of mucin production from goblet cells.

Auxiliary agents, such as compounds that will protect the active compound from acid destruction in the stomach or facilitate the absorption of the active compound into the bloodstream can also be incorporated into the pharmaceutical composition, if necessary or desirable. Other auxiliary agents commonly used in ophthalmic preparations, such as aloe vera gel or other agents that improve ocular tolerance are also beneficially included in the compositions described herein. Absorption can also be enhanced by delivering the active compound by means of a liposome or nanoparticle carrier.

The compounds of Formula I, above, along with any supplementary active agent(s) may be administered using any amount and any route of administration effective for the treatment or prophylaxis of dry eye disorders. Thus, the expression "therapeutically effective amount", as used herein, refers to an amount of a compound of Formula I, above, which is both non-toxic and sufficient to relieve or eliminate dry eye symptoms. The effective amount of a given compound and its optimal mode of administration are determined in accordance with established medical standards, taking into account the species, age, gender, weight and health of the patient, the nature and severity of the dry eye disorder being treated, the particular compound being administered, its route of administration, the judgment of the attending medical professional, and the like. Similarly, the expression "prophylactically effective amount", as used herein, refers to an amount of a compound or composition described herein which is sufficient to protect the recipient against development of a dry eye disorder.

The compounds of the invention are preferably formulated in dosage unit form for ease of administration and uniformity of dosage. "Dosage unit" form as used herein refers to a physically discrete unit of one or more compounds described herein which is appropriate for the patient to be treated. Each dosage should contain the quantity of active agent calculated to produce the desired therapeutic or prophylactic effect when administered as such, or in association with the selected pharmaceutical carrier medium. The appropriate quantity of therapeutic agent to be included in a specific dose form, so as to provide such an effect can be determined by procedures well known in the art, and should be such as to achieve an appreciable beneficial change over time in the disorder being treated or to preclude manifestation of symptoms in the first instance.

The compounds of the invention may be administered topically, enterally or parenterally, such as by subcutaneous injection, intramuscular injection, intraperitoneal injection, intravenous infusion, transdermal patch, or the like, depending on the nature of the condition being treated. Oral, topical ocular (eye drops, eye wash) are particularly preferred, provided the dosage is capable of generating plasma and/or target tissue levels of the compound that are therapeutically active. Those skilled in the art can readily measure the levels of a small molecule therapeutic or prophylactic agent in plasma or target tissue. The concentration of the active agent in these samples can be compared with a predetermined effective amount established in vitro to assess its efficacy.

The compounds of the invention will typically be administered once per day or up to 4-5 times per day, depending upon the particular compound(s) chosen. While a dosing schedule of once-a-day is preferred, a more frequent dosing schedule may be required. However, the exact regimen for administration of the compound(s) and compositions described herein will necessarily be dependent on the needs of the individual patient being treated, the type of treatment administered and the judgment of the attending physician. As used herein, the term "patient" refers to animals, including mammals, preferably humans.

The therapeutic method and prophylactic method of the invention will normally include medical follow-up to determine or assess whether the intended effect is being brought about in the patient undergoing treatment with the compound(s) described herein.

The following example describes the invention in further detail. This example is provided for illustrative purposes only and should in no way be construed as limiting the invention or its applicability in treating dry eye conditions.

EXAMPLE 1

Sprague-Dawley male rats (7 weeks old, average weight=444 g) were treated with subcutaneous (SC) scopolamine hydrobromide in normal saline (n=30, 25 mg/kg injected 3× per day) or nothing (n=4). Scopolamine treated animals received either (a) 50 mM meglumine in the drinking water (n=10), (b) a 3× daily eyemist containing 2% by weight of meglumine hydrochloride (n=10) or (c) a 3× daily eyemist of normal saline (n=10). Treatment was for 4.5 weeks. One animal receiving scopolamine and the meglumine eyemist died just prior to the end of the study, and the eye tissues were not analyzed. Animals were euthanized and the eye orbit and surrounding tissue from both eyes were removed and placed in formalin. Tissues were embedded in paraffin, thin sections prepared, and stained with periodic acid Schiff to more easily visualize the goblet cells.

Table 1, below, shows independent, blinded ratings of the goblet cell densities. Animals not treated with scopolamine or with scopolamine and a saline eyemist had the lowest levels of goblet cells. Animals treated with scopolamine and oral meglumine had the highest levels of goblet cells. The difference in goblet cell density between the untreated animals and those treated with oral meglumine was significant for one grader (p=0.04) and approached significance for the other (p=0.07). The meglumine eye mist referred to in Table 1 was obtained from Piedmont Chemical Industries (High Point, N.C.).

FIG. 1 shows examples of goblet cell densities for eye tissues from animals treated with scopolamine and either a saline eyemist (panels A and B) or oral meglumine (panels C and D). The animals on oral meglumine (panels) have more extensive regions containing goblet cells.

TABLE 1

| | Goblet Cell Rating (Avg ± SD) | |
|---|---|---|
| | Grader 1 | Grader 2 |
| oral meg | 2.40 ± 0.75 | 2.22 ± 0.93 |
| meg eyemist | 1.95 ± 0.83 | 1.91 ± 0.82 |
| saline eyemist | 1.67 ± 1.03 | 1.26 ± 0.84 |
| control (no scopolamine) | 1.63 ± 1.06 | 1.59 ± 0.97 |
| t-test | | |
| oral meg vs control | 0.04 | 0.07 |

Grader ratings for thin sections of rat eye tissues from animals with various treatments. Rating 1 = few goblet cells and rating 5 = many goblet cells.

A number of patent and non-patent publications are cited in the foregoing specification in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing specification. The present invention is, therefore, not limited to the particular embodiments described and/or exemplified, but is capable of considerable variation and modification without departure from the scope of the appended claims.

REFERENCES

Deplancke, B. and H R Gaskins. (2001) Microbial modulation of innate defense: goblet cells and the intestinal mucus layer. Am J Clin Nutr 73(suppl):1131S-1141S.

Fujihara, T., T. Murakami, H. Fujita, M. Nakamura, and K. Nakata. (2001) Improvement of corneal barrier function by the P2Y$_2$ agonist INS365 in a rat dry eye model. Invest Ophthalmol 42:96-100.

Gipson, I. K., Y. Hori and P. Argueso. (2004) Character of ocular surface mucins and their alteration in dry eye disease. Ocul Surf 2:131-148.

Jumblatt, J. E. and M. M. Jumblatt. (1998) Regulation of ocular mucin secretion by P2Y$_2$ nucleotide receptors in rabbit and human conjunctiva. Exp Eye Res 67:341-346.

Kunert, K., S. A. S. Tisdale, I. K. Gipson. (2002) Goblet cell numbers and epithelial proliferation in the conjunctiva of patients with dry eye syndrome treated with cyclosporine. Arch Ophthalmol 120:330-337.

Lemp, M. A. (1995) Report of the National Eye Institute/Industry workshop on clinical trials in dry eyes. CLAO J. 21(4):221-232.

Moss, S. E., R. Klein, and B. E. K. Klein. (2000) Prevalence of and risk factors for dry eye syndrome. Arch Ophthalmol. 118:1264-1268.

Nakamura, M., K. Endo, K. Nakata, and T. Hamano. (1998) Gefarnate increases PAS positive cell density in rabbit conjunctiva. Br J Ophthalmol 82:1320-1323.

Pelit A., T. Bagis, F. Kayaselcuk, D. Dursun, Y. Akova and P. Aydin (2003) Tear function tests and conjunctival impression cytology before and after hormone replacement therapy in postmenopausal women. Eur J Ophthalmol 13:337-342.

Shimotoyodome, A., S Megurok T Hase, I Tokimitsu and T Sakata. (2000) Decreased colonic mucus in rats with loperamide-induced constipation. Comp Biochem Physiol—Part A Molecular and Integrative Physiology. 126:203-212.

Srinivasan, S. and A. R. Siomovic. (2007) Sjogren syndrome. Compr Ophthalmol Update 8:205-12.

Sullivan, D. A. (2004) Tearful relationships? Sex, hormones, the lacrimal gland, and aqueous-deficient dry eye. Ocul Surf 2:92-123.

Tauber, J. (1998) Lacrimal Gland, Tear Film and Dry Eye Syndromes 2. J. Adv. Exp. Med. Biol., 438: 969.

Toda I. (2007) LASIK and dry eye. Compr Ophthalmol Update 8:79-85.

Zoukhri, D. (2006) Effect of Inflammation on lacrimal gland function. Exp Eye Res 82:885-898.

What is claimed is:

1. A method for treating a dry mucus membrane disorder selected from the group consisting of dry eyes, dry mouth and constipation in a patient in need thereof by administering to said patient a therapeutically effective amount of a therapeutic agent that increases mucin production in said patient, said therapeutic agent consisting essentially of a compound of the formula:

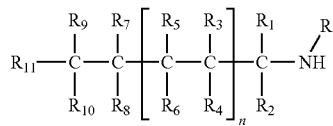

(I)

wherein R represents a substituted or unsubstituted alkyl ($C_1$-$C_4$), said alkyl substituents being selected from the group of hydroxy, carboxy, and phosphono substituents;

$R_1$ and $R_2$ are the same or different and represent a radical selected from the group consisting of hydrogen and hydroxymethyl radicals;

$R_3$ and $R_4$ are the same or different and represent a hydrogen or hydroxy radical;

$R_5$ and $R_6$ are different and represent either a hydrogen or hydroxy radical;

$R_7$ and $R_8$ are different and represent either a hydrogen or hydroxy radical;

$R_9$, $R_{10}$ and $R_{11}$ are the same or different and represent a radical selected from the group consisting of hydrogen, alkyl ($C_1$-$C_2$), hydroxyalkyl and hydroxy radicals;

n represents either 0 or 1, the pharmaceutically acceptable salts and isomeric forms of said compound.

2. The method of claim 1, wherein said dry mucus membrane disorder is dry eyes.

3. The method of claim 1, wherein said therapeutic agent is meglumine or a pharmaceutically acceptable salt thereof.

4. The method of claim 1, wherein said dry mucus membrane disorder is selected from the group consisting of dry eyes and dry mouth.

5. The method according to claim 1 wherein said compound is administered in the form of a composition further comprising a pharmaceutically acceptable carrier.

6. The method according to claim 5, wherein the compound of formula I is present in said composition in an amount of at least 0.0001% to about 10.0% by weight, based on the total weight of the composition.

7. The method according to claim 5, wherein the compound of formula I is present in an amount between 0.001% and 0.01%.

8. The method according to claim 1, wherein said patient is a mammal.

9. The method according to claim 1, wherein said patient is a human.

10. The method according to claim 1, wherein said compound is orally administered.

11. The method according to claim 1, wherein said compound is topically administered.

* * * * *